United States Patent [19]

Berman et al.

[11] Patent Number: 5,743,843
[45] Date of Patent: Apr. 28, 1998

[54] METHOD FOR THERAPEUTIC BLOOD CONDITIONING

[76] Inventors: Michael F. Berman, 19 Berkshire Cir., Ansonia, Conn. 06401; Randy Boncek, 46 Florence St., East Haven, Conn. 06513

[21] Appl. No.: 505,373

[22] Filed: Jul. 21, 1995

[51] Int. Cl.⁶ .................................................. A61B 17/52
[52] U.S. Cl. ............................... 600/9; 600/15; 128/898
[58] Field of Search .................... 600/9, 16, 15; 128/898

[56] References Cited

U.S. PATENT DOCUMENTS

| | | |
|---|---|---|
| 4,587,956 | 5/1986 | Griffin et al. .......................... 600/15 |
| 5,226,020 | 7/1993 | Li et al. .............................. 600/15 X |
| 5,304,111 | 4/1994 | Mitsuno et al. ..................... 600/15 X |
| 5,389,981 | 2/1995 | Riach, Jr. ............................. 600/9 X |

*Primary Examiner*—Jennifer Bahr
*Assistant Examiner*—Ryan Carter
*Attorney, Agent, or Firm*—Charles F. Blaich

[57] ABSTRACT

A method to improve the solubility, dispersability and buffering capacity of blood by exposing a patient's blood to a constant mono-polar magnetic field of at least one tesla utilizing the patient's circulatory system to pass blood through the imposed magnetic field.

2 Claims, 1 Drawing Sheet

METHOD FOR THERAPEUTIC BLOOD CONDITIONING

BACKGROUND OF THE INVENTION

The human body's circulatory system is often fraught with problems. This to a large extent related to loss of solubility and dispersability of various blood components. This results in the gradual precipitation and adhesion of various chemical complexes and salts onto the inner walls of arteries and veins. Common pathological examples of this action include arteriosclerosis, which can lead to renal and heart failure. The renal failure is caused by blockage of glomerulus and tubuli, arterial blockage caused by plating out of calcium complexes and fatty polymer deposits. Metabolism and transport rates of various blood components also can be affected by solubility factors.

Various chemical means (drugs) have and are being devised to alter the production of cholesterol and other lipid fractions by the liver but in doing so almost invariably offset the balance of other components which are essential to body function.

Blood as well as other body fluids are composed of dispersed and soluble phases. Each of these phases are made up of a very large number of ions, monomers, oligomers and polymers in an aqueous medium. Virtually all of these polar and ionized groups fall into a class of chemicals termed as zwitterions, electrolytes and polar molecules. Furthermore, these components can be separated by their difference in electrostatic attraction towards an electrically charged pole when embedded in a polymeric gel matrix under high voltage potential. This method is known as electrophoresis. The electrolytes can possess either a net positive or negative charge. Zwitterions possess localized opposite net charges on the same molecule. The majority of anions in body fluids are 1) carbonate, 2) bicarbonate, 3) phosphate, 4) pyrophosphate, 5) chloride and 6) hydroxide. The carbonate and bicarbonates act as extracellular buffers and the phosphates/pyrophosphates act as intracellular buffers. The majority of cations in body fluids are: 1) sodium, 2) potassium, 3) calcium, 4) iron, 5) zinc and 6) magnesium. Among their numerous functions are the maintenance of electrolyte balance and coordination of enzymatic catalysis. The majority of zwitterions are 1) amino acids, 2) proteins (i.e. globular proteins), and 3) lipoprotein complexes.

The role of electrolytes is essential for the function of the human body and its complex chemistry since there are almost no metabolic processes which are not dependent on or affected by electrolytes. Among the essential functions dependent upon electrolytes are maintenance of osmotic pressure between intracellular and extracellular fluids, maintenance of proper acid/base balance (buffering capacity), regulation of muscle physiology, direct involvement in oxidation-reduction or electron transfer reactions which take place in enzyme reactions.

The instant invention directly affects the above solubilities, dispersabilities, and buffering capacity of blood components by the application of a constant polar state of nonelectrical magnetic fields to the blood flowing through a blood vessel. The magnetic field(s) are applied close to or perpendicular to the direction of blood flow. The applied field affects the overall solubility and dispersability of the various blood components.

| PRIOR ART | | |
|---|---|---|
| U.S. Pat. No. | Date of Issue | Inventor(s) |
| 96,044 | October, 1869 | Smith |
| 1,634,373 | July, 1927 | Mann |
| 4,850,340 | July, 1989 | Onishi |
| 4,994,014 | February, 1991 | Gordon |
| 5,067,940 | November, 1991 | Liboff et al. |

Smith describes a "Galvanic Apparatus" to surround the patient's body to induce magnetism into the patient.

Mann teaches the use of "heat, vibration and eddy currents for the purpose of treating the human body". Again the effect of the eddy current and or "alternating current" field are not disclosed.

Onishi teaches "A therapeutic apparatus generates magnetic field which treats pain, stiffness of body and other ailments of patients through enhancing blood circulation by continuous application of an alternating magnetic field to the affected portion of the body." Onishi claims the magnetic generation of heat in the body enhances blood flow.

Gordon teaches the introduction of magnetic particles into the blood then by determining the resonant frequencies of tissue, cancer cells, or diseased cells applying a tuned external electromagnetic field to achieve biophysical alteration including the stimulation of intracellular production of interleukins or like substances.

Liboff et al. teaches the use of tuned magnetic fields to control growth characteristics of living tissue by inducing measurable generated voltage in tissue, bone, etc.

In addition to the above patent art, attention is drawn to a paper entitled Applied Fields for Energy Conservation; Water Treatment and Industrial Applications by R. S. Reimers, S. F. Bock and Lu Ann E. White completed at Tulane University and the United States Department of Energy which reports the effects of polar molecules and electrolytes in solution when exposed to magnetic fields.

SUMMARY OF THE INVENTION

In its simplest form the instant invention is a single pole nonalternating field magnet which surrounds and is affixed to a patient's extremity (i.e. arm or leg). The magnet can also be affixed temporarily or permanently to a blood vessel that precedes a partially blocked region of blood circulation. As the blood flows through the magnetic field, polarizable molecules and electrolytes orient themselves with the magnetic field in an increased ordered fashion. Consequently, solubility of these molecules increase. Hence the probability of plaque or clot formation on the surface of blood vessel walls also decrease due to the effect of a shift in solubility constants and mass action equilibrium.

Continued exposure of the blood to a constant either northpole or southpole, magnetic field but never both poles simultaneously. This results in magnetic conditioning over a long period of time thus the desired physiological effects take place gradually over a period of time. The same effect of a single pole magnetic field over an organ site or its blood supply for example, kidneys, exposing them and surrounding tissue and their blood supply to solubilize deposits therein.

In the past, magnets that possessed about one Tesla or greater magnetic field were limited to AC type electromagnets. Since the field of such magnets reverses depending upon the positive or negative phase of the AC cycle, the effect of such change of fields caused disorientation rather than orientation of dipoles which is a criterion for achieving the therapeutic effect of the instant invention. With current synthetic technology, it is possible to develop very powerful magnetic fields (1–100 Tesla) with relatively light weight material (1 kg) and in flexible members which permit wrapping around an extremity.

DETAILED DESCRIPTION

Figure 2:
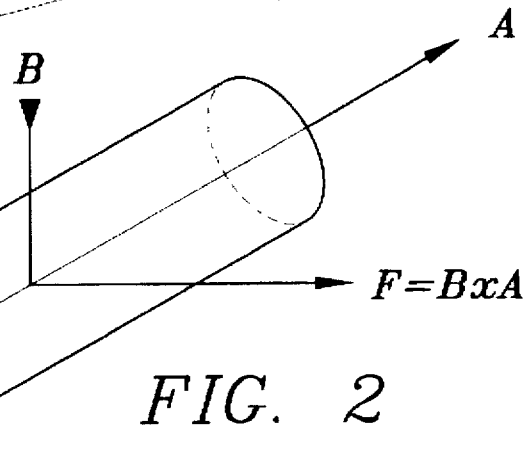
FIG. 2 illustrates the vectors of polar liquid flowing through a magnetic field.

In order to exert an effect of a magnetic field on a polarizable liquid such as blood the liquid must flow through a magnetic field. The influence of such a magnetic field produces a force F on the molecules within the polarizable liquid. This resulting force is the cross product of two vectors. The first, magnetic field vector B and second velocity vector A the molecules flowing through a magnetic field (FIG. 2) In general the velocity vector A and magnetic vector B generate a third vector F which result is normal to the other two vectors. This third vector F is the resultant cross product of the velocity vector and a magnetic field vector and is known as magnetic force vector or Lorenztz force. It is this vector that polarizes a molecule moving through a magnetic field. This act of polarization is the change in electron density of a molecule rendering the molecule or functional group more polar than before. Furthermore, relatively nonpolar molecular moieties such as lipids will develop an induced dipole moment in the magnetic field which promotes greater chemical interaction with a solvent. It should also be pointed out that the molecular motion or blood flow (velocity vector) and magnetic field (magnetic field vector) are both required for this effect. Hence it is clear that increasing either or both vector components will result in an increase in molecular polarization and overall solubility.

In order for the above effect to result in any physiological benefit, a minimum effective magnetic field of one Tesla from a north and/or south pole magnet should be used around an extremity extending parallel to the blood flow direction. The magnetic matrix material should be flexible and durable for comfortable but accurate orientation of the magnet. Magnetic conditioning implies that the desired physiological effects take place gradually and after a period of time. It is possible to treat specific vascular sites (i.e. organs, muscle) by locating the appropriately pole oriented magnets and their magnetic field before or over the organ site or to its blood supply, for example the kidneys, treating the same to solubilize deposit therein. Further, a magnet may be placed around a patient's neck to directly condition the blood flow to the brain via the carotid arteries thus assisting in the breakup of blood vessel deposits near or in the brain.

Figure 1:
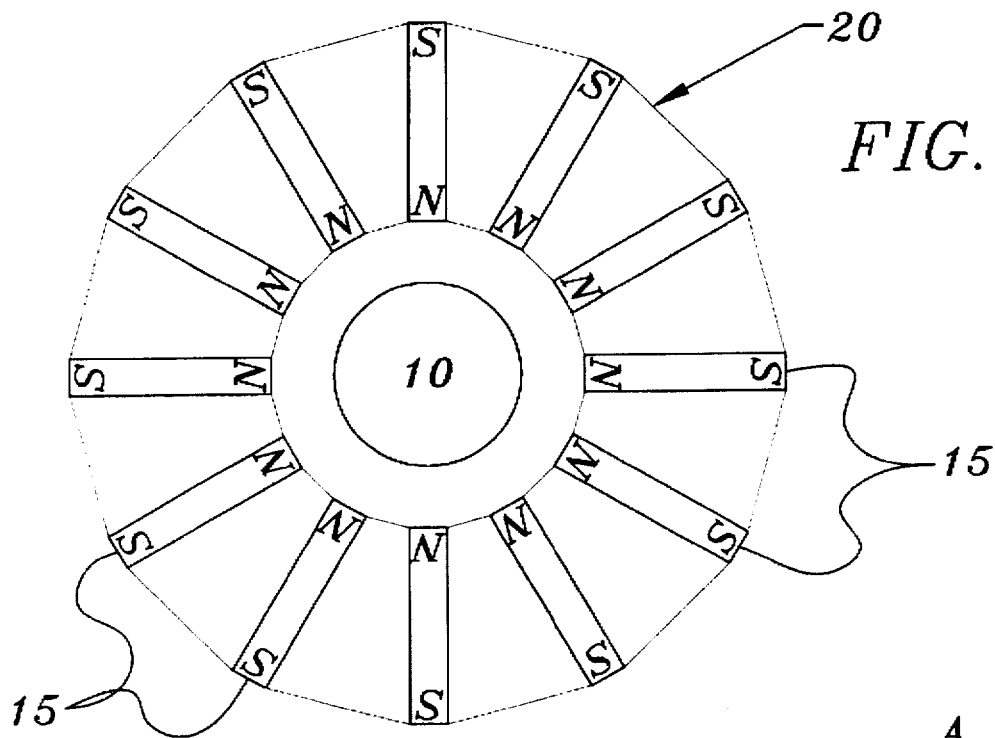
FIG. 1 illustrates a cross section of an extremity surrounded by numerous magnets.
Figure 3:
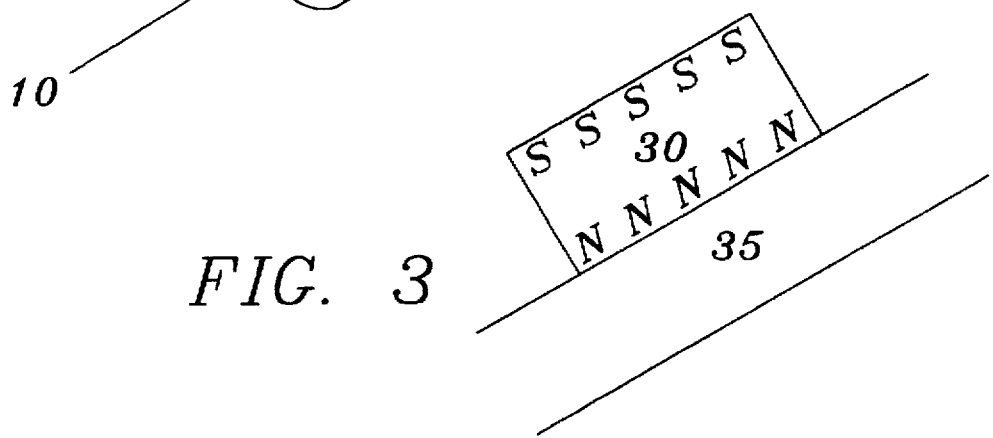
FIG. 3 illustrates single magnetic orientation of a lineal magnet adjacent to a patients extremity.

A magnetic field which is useful in the instant invention may be made of several lineal magnets with common north south orientation shown in FIG. 1 which is a cross section of a cylindrical magnet 20 around an extremity 10. The cylindrical magnet is composed of a number of lineal magnets 15 which extend in radial fashion around the extremity 10 forming a constant orientation magnetic field around the extremity. As shown diagramatically in FIG. 2 as blood flows through extremity 10 a magnetic field is generated by the orientated magnets of FIG. 1. The form of the magnet 30 FIG. 3 may also be lineal as long as there is a single orientation, i.e. either the north or the south pole being perpendicularly directed at a patient's extremity 35 so that blood flow passing through the magnetic field generated by the magnet establishes the vector effect. The blood is subject to the polarizing force F as previously described. An indication of the effect of such a magnetic field is shown in an experiment wherein 1% low fat milk was diluted with distilled water to a 1:400 ratio. This liquid was pumped through a vinyl tube with a rotary pump at approximately 10 liter/minute rate. A 2 Tesla magnet was placed parallel to and in engagement with the tube. The liquid being pumped was maintained at less than 5° C. to prevent souring and pumped for 24 hours. A number of experiments were conducted which resulted in the following turbidity readings. (Nepholometer Turbidity Units)

| Trial No. | Magnetically Treated | Non Magnetically Treated |
| --- | --- | --- |
| 1 | 17 NTU | 67 NTU |
| 2 | 17 NTU | 67 NTU |
| 3 | 17 NTU | 67 NTU |

Each of the above conditioned samples were filtered through a 0.45 micron filter with vacuum and turbidity determined. (nonsoluble portion)

| Trial No. | Filtrate Turbidity Magnetically Treated | Filtrate Turbidity Non Magnetically Treated |
| --- | --- | --- |
| 1 | 6.8 NTU | 25 NTU |
| 2 | 6.9 NTU | 24 NTU |
| 3 | 6.8 NTU | 26 NTU |

A second experiment was conducted to determine the solubility of the calcium in the magnetic field exposed and nonexposed dilute milk matrix. The base milk dilutions had 660 ppm.±5 ppm. calcium (control). After exposure to the magnetic field the exposed milk was vacuum filtered through a 0.45 micron filter and the organic portion of the filtrate was determined. The following was found:

| | |
| --- | --- |
| Calcium before exposure (control) | 660 + 5 ppm. |
| Calcium after magnetic field exposure | 512 ppm |
| Calcium without magnetic exposure | 336 ppm. |

Both dilute milk systems were pumped through the system previously described. The solubility of the milk solids in the magnetically exposed sample indicates that a significant portion of the calcium in the milk solids which are mainly lipids and other fatty organic molecules was solubilized—not being filtered out on the 0.45 micron filter.

Other benefits and applications of magnetic therapeutic blood conditioning include but are not limited to:

Increased blood gas transfer efficiency ($O_2/CO_2$).

Greater buffering capacity.

Greater healing rate of damaged tissue and "open wound" patients. This includes a more rapid decimation of scar tissue.

Enhanced drug delivery via plasma and/or cells.

Increase in red corpuscle life span which aids in defending against infections.

Enhanced electrolyte transfer in nerve cells for the possible treatment of neural or nervous disorders or diseases including Alzheimer's disease.

The foregoing details are exemplary only and are not illustrative of the principles of this invention and are not to be interpreted to limit the scope of the invention.

What is claimed is:

1. A method for improving the solubility, dispersability, and buffering capacity of polar blood components comprising exposing a patient's blood to a minimum magnetic force field of one (1.) Tesla generated with a lineal single pole oriented magnet with a minimum length of 7.5 cm, placing the lineal magnet in parallel relationship with and immediately adjacent to a patient's extremity having blood vessels through which the blood including the polar blood components is flowing, the polar blood components orienting as the blood passes through the blood vessels and the magnetic force field, thereby having improved solubility, dispersability, and buffering capacity.

2. A method for improving the solubility, dispersability, and buffering capacity of polar blood components comprising exposing a patient's blood to a minimum magnetic force field of one (1.) Tesla generated with a cylindrical magnet made up of multiple single pole magnets having common polar orientation around a cylinder, placing the cylindrical magnet around a patient's extremity having blood vessels through which the blood including the polar blood components is flowing, the polar blood components orienting while passing through the magnetic force field, thereby having improved solubility, dispersability, and buffering capacity.

* * * * *